(12) United States Patent
Kolari et al.

(10) Patent No.: US 9,723,833 B2
(45) Date of Patent: Aug. 8, 2017

(54) BIOCIDE COMPOSITION AND METHOD FOR TREATING WATER

(71) Applicant: KEMIRA OYJ, Helsinki (FI)

(72) Inventors: Marko Kolari, Vantaa (FI); Jukka Rautiainen, Espoo (FI)

(73) Assignee: KEMIRA OYJ, Helsinki (FI)

( * ) Notice: Subject to any disclaimer, the term of this patent is extended or adjusted under 35 U.S.C. 154(b) by 0 days.

(21) Appl. No.: 14/760,389

(22) PCT Filed: Jan. 27, 2014

(86) PCT No.: PCT/FI2014/050060
§ 371 (c)(1),
(2) Date: Jul. 10, 2015

(87) PCT Pub. No.: WO2014/114851
PCT Pub. Date: Jul. 31, 2014

(65) Prior Publication Data
US 2015/0351383 A1   Dec. 10, 2015

(30) Foreign Application Priority Data

Jan. 25, 2013  (FI) .................................. 20135077

(51) Int. Cl.
*A01N 25/02* (2006.01)
*A01N 37/34* (2006.01)
*A01N 37/36* (2006.01)

(52) U.S. Cl.
CPC ............. *A01N 25/02* (2013.01); *A01N 37/34* (2013.01); *A01N 37/36* (2013.01)

(58) Field of Classification Search
CPC ................................ A01N 25/02; A01N 37/34
USPC ................................................. 514/553, 528
See application file for complete search history.

(56) References Cited

U.S. PATENT DOCUMENTS

| RE24,184 E | 7/1956 | Sanders et al. |
|---|---|---|
| 4,420,484 A | 12/1983 | Gorman |
| 4,950,420 A | 8/1990 | Svarz |
| 2009/0181850 A1 | 7/2009 | Stern et al. |

FOREIGN PATENT DOCUMENTS

| CN | 101453897 A | 6/2009 |
|---|---|---|
| CN | 101720786 A | 6/2010 |
| EP | 1219172 A1 | 7/2002 |
| EP | 2147599 A1 | 1/2010 |
| GB | 1321404 | 6/1973 |
| GB | 1457509 A | 1/1976 |
| GB | 1433029 | 4/1976 |
| WO | 03/003832 A1 | 1/2003 |
| WO | 03/067989 A1 | 8/2003 |
| WO | 2007/123790 A1 | 11/2007 |
| WO | 2008/049616 A1 | 5/2008 |
| WO | 2012/158435 A1 | 11/2012 |

OTHER PUBLICATIONS

DOW Antimicrobial 7287 and DOW Antimicrobial 8536: The fast-acting, broad-spectrum biocides iwth low environmental impact. Jun. 27, 2002 Retrieved on Apr. 14, 2014 from the Internet URL:http://msdssearch.dow.com/PublishedLiteratureDOWCOM/dh_0043/0901b80380043c9e.pdf.
Anonymous: DBNPA of biocide product from SinoHArvest DBNPA manufacturer. Jan. 6, 2009 pp. 1-2. Retrieved from the Internet URL: https:/web.archive.org/web/2009010604207 http://www.sinoharvest.com/products/DBNPA.shtml. retreived on Apr. 14, 2014.
Search report. National Board of Patents and Registration of Finland date Nov. 20, 12013.
State Intellectual Property Office of People's Republic China, Search Report dated Jun. 15, 2016 for CN Appln. No. 201480006004.9.
European Patent Office, Communication pursuant to Article 94(3) EPC for EP14710935.9 issued on Sep. 16, 2016.

*Primary Examiner* — Kristin Vajda
(74) *Attorney, Agent, or Firm* — Berggren Inc.

(57) ABSTRACT

The present invention provides a biocide composition comprising a biocide and a carrier, wherein the biocide is soluble in the carrier. The carrier may comprise polyethylene glycol ester. The present invention also provides a method for controlling biofilms by eliminating and/or preventing microorganisms in an aqueous environment.

15 Claims, 1 Drawing Sheet

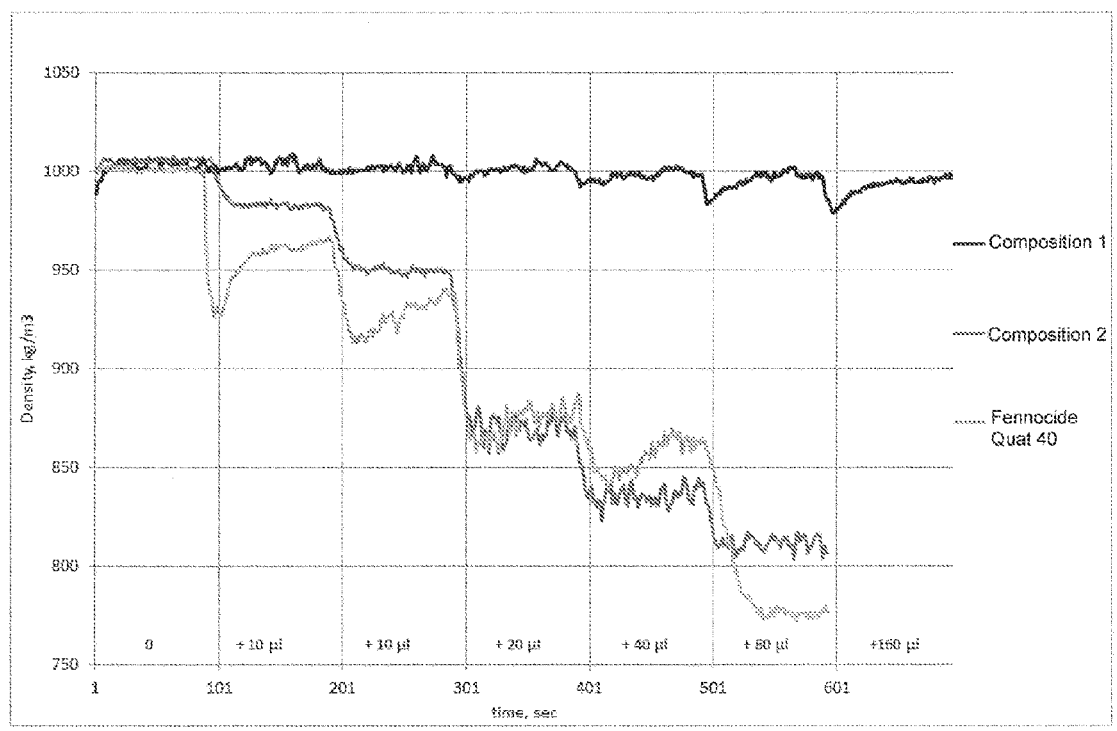

BIOCIDE COMPOSITION AND METHOD FOR TREATING WATER

This application is a national application of PCT-application PCT/FI2014/050060 filed on Jan. 27, 2014, which claims priority of the Finnish national application number FI20135077 filed on Jan. 25, 2013, both of which are incorporated herein by reference.

FIELD OF THE INVENTION

The present invention relates to a biocide composition comprising a biocide and a carrier. More particularly the carrier comprises a polyethylene glycol ester, such as tall oil fatty acid polyethylene glycol ester. The present invention also relates to methods for treating water and controlling biofilms by eliminating microorganisms and/or preventing the growth of microorganisms.

BACKGROUND

Water-intensive processes, such as papermaking and cooling water processes, are offering a fertile environment for microbiological growth. Therefore biocidal treatments are often necessary in various water-containing processes. The target of biocidal treatments in industry is not usually a complete sterilization, but a contribution for finding a stable, dynamic balance of microbial growth on an acceptable and cost-efficient level. The prior art relates to wide variety of biocides in different kind of applications within water-intensive industries, paper industry being one of the biggest. Within that area it is estimated that a part of the applications are currently using technologies that could be replaced if more effective biofilm-control technology based on targeted biocides could be found.

A biofilm is an aggregate of microorganisms in which cells adhere to each other on a surface. These adherent cells are frequently embedded within a self-produced matrix of extracellular polymeric substance (EPS). Biofilm EPS, which is also referred to as slime, is a polymeric conglomeration generally composed of extracellular DNA, proteins, and polysaccharides. Biofilms may form on living or non-living surfaces and can be prevalent in natural, industrial and hospital settings. The microbial cells growing in a biofilm are physiologically distinct from planktonic cells of the same organism, which, by contrast, are single-cells that may float or swim in a liquid medium.

Formation of a biofilm begins with the attachment of free-floating microorganisms to a surface. These first colonists adhere to the surface initially through weak, reversible adhesion via van der Waals forces. If the colonists are not immediately separated from the surface, they can anchor themselves more permanently using cell adhesion structures such as pili. Some species are not able to attach to a surface on their own but are often able to anchor themselves to the EPS matrix or directly to earlier colonists. It is during this colonization that the cells are able to communicate via quorum sensing using such signals as AHL compounds. Once colonization has begun, the biofilm grows through a combination of cell division and recruitment. The final stage of biofilm formation is known as development, and is the stage in which the biofilm is established and may only change in shape and size. The development of a biofilm may allow for an aggregate cell colony (or colonies) to be increasingly antibiotic resistant.

Biofilms contribute in many problems in aqueous industrial systems, such as recirculating systems, e.g. paper machines or cooling systems. The build-up of surface contaminants such as biofilms can cause problems such as poor heat transfer, high energy consumption, corrosion, increased maintenance expenditures, shortened system life, high operating costs, unscheduled down time of the equipment etc.

A biocide is an antimicrobial chemical substance which can deter, render harm-less, or exert a controlling effect on any harmful organism. Biocides are commonly used in medicine, agriculture, forestry, and industry. A biocide may be further classified as a germicide, an antibiotic, an antibacterial, an antiviral, an antifungal, an antiprotozoal or an antiparasite.

Most of the current biocides have been developed for the control of planktonic bacteria. At the generally used low concentrations such biocides are not very effective against biofilms. The sheath or matrix formed by EPS-producing microorganisms makes them tolerate higher dosages of most of the common biocides. Using high doses of biocides may cause other problems, such as corrosion of the equipment. Also, because biocides are intended to kill living organisms, increasing dosages of biocidal products increases risks for human health and welfare.

There is a need for better biocides which can be used against biofilms on surfaces. They should be able to be targeted to the biofilms and advantageously also be able to penetrate the biofilm and kill the biofilm organisms. Such biocides should be effective also at low doses.

SUMMARY OF THE INVENTION

In the present invention it was surprisingly discovered that when using a suitable agent, such as a defoamer composition, as a biocide carrier a multifunctional product was obtained. The biocide could be solubilized and effectively targeted to biofilms on surfaces. The composition also prevented foaming, which is detrimental for most of the water-intensive industrial processes. The ability to target on surfaces provides means for preventing biofilm and preventing or inactivating any preformed biofilms at a lower amount of biocidal active used than with existing technologies.

The present invention provides a biocide composition comprising a biocide and a carrier, wherein the biocide is soluble in the carrier.

The present invention also provides a method for controlling biofilms by eliminating and/or preventing microorganisms in an aqueous environment, comprising providing said biocide composition, and dosing said biocide composition to the aqueous environment.

It is an advantage of the present invention that the biocides may be targeted to biofilms on surfaces.

It is another advantage of the present invention that the biocides can penetrate the biofilm and attack the microorganisms in the biofilm matrix. The biocide composition of the invention provides biocide solubilization which makes this possible.

It is still another advantage of the present invention that the biocide composition prevents foaming.

It is still another advantage of the present invention that the biocide activity is pro-longed. This enables an effective and increased biofilm control in a more sustain-able way.

It is still another advantage of the present invention that overall need for toxic biocidal compounds used is reduced, i.e. lower doses can be used.

It is still another advantage of the present invention that the composition is stable. It has a substantial shelf-life, for example the biocide retains its activity for at least several weeks or months.

BRIEF DESCRIPTION OF THE FIGURES

FIG. 1 shows test results for foaming tendency of Composition 1 and Composition 2 with dosages of 10 μl to 160 μl, using Fennocide Quat 40 as a reference.

DETAILED DESCRIPTION OF THE INVENTION

The present invention provides a biocide composition comprising a biocide and a carrier, wherein the biocide is soluble in the carrier.

The biocide may be any suitable biocide (antimicrobial agent) able to kill the microorganisms, such as the biofilm-forming microorganisms. The biocide may be soluble to water, it may have low solubility to water, or it may even be non-water-soluble. However, the biocide should be soluble in the carrier. Generally the biocide composition contains at least 2% (w/w) of the biocide (antimicrobial agent). In one embodiment the biocide composition contains about 5-50% (w/w) of the biocide. In one embodiment the biocide composition contains about 10-20% (w/w) of the biocide. In one embodiment the biocide composition contains about 13-17% (w/w) of the biocide. In one specific example the biocide composition contains about 15% (w/w) of the biocide.

The biocides may be generally divided into two categorical groups: oxidizing and non-oxidizing (or conventional) biocides. The non-oxidizing biocides include biocides such as DNBPA, other bromine-containing biocides, glutaraldehyde, isothiazolones etc. One example of suitable biocides for use in the compositions of the invention includes non-oxidizing biocides. The biocides may also be divided into groups by function mechanisms. The electrophiles include oxidants, such as halogens and peroxy compounds, and electrophiles, such as formaldehyde, formaldehyde-releasers, isothiazolones, Bronopol and Cu, Hg and Ag. The membrane active biocides include lytic biocides, such as quats, biguanides, phenols and alcohols, and protonophores, such as parabens, weak acids and pyrithiones.

Examples of non-oxidizing biocides include glutaraldehyde, 2,2-dibromo-3-nitrilopropionamide (DBNPA), 2-bromo-2-nitropropane-1,3-diol (Bronopol), 5-chloro-2-methyl-4-isothiazolin-3-one (OMIT), 2-methyl-4-isothiazolin-3-one (MIT), a mixture of OMIT and MIT, 1,2-dibromo-2,4-dicyanobutane, bis(trichloro-methyl)sulfone, 2-bromo-2-nitrostyrene, 4,5-dichloro-1,2-dithiol-3-one, 2-n-octyl-4-isothiazolin-3-one, 1,2-benzisothiazolin-3-one, ortho-phthalaldehyde, quaternary ammonium compounds ("quats") such as n-alkyl dimethyl benzyl ammonium chloride, didecyl dimethyl ammonium chloride (DDAC) or alkenyl dimethylethyl ammonium chloride, guanidines, biguanidines, pyrithiones, carbamates, 3-iodopropynyl-N-butylcarbamate, phosphonium salts such as tetrakis hydroxymethyl phosphonium sulfate (THPS), 3,5-dimethyl-1,3,5-thiadiazinane-2-thione (Dazomet), 2-(thiocyanomethylthio)benzothiazole, methylene bisthiocyanate (MBT), and combinations thereof.

Examples of oxidizing biocides include chlorine, alkali and alkaline earth hypo-chlorite salts, hypochlorous acid, chlorinated isocyanurates, bromine, alkali and alkaline earth hypobromite salts, hypobromous acid, bromine chloride, chlorine dioxide, ozone, hydrogen peroxide, peroxy compounds, such as peracetic acid, performic acid, percarbonate or persulfate salts, halogenated hydantoins, e.g., monohalodimethylhydantoins such as monochlorodimethylhydantoin, or dihalodimethylhydantoins such as chlorobromodimethylhydantoin, monochloramines, monobromamines, dihaloamines, trihaloamines, active halogen compounds reacted with other nitrogenous compounds such as urea, and combinations thereof.

Most common types of non-oxidizing biocides being used in the pulp and paper making processes include 2-bromo-2-nitropropane-1,3-diol, 5-chloro-2-methyl-4-isothiazolin-3-one, DBNPA, n-octyl-isothiazolin-3-one, MBT, quaternary ammonium compounds, THPS and glutaraldehyde.

In one embodiment the biocide is selected from the group consisting of glutaraldehyde, 2,2-dibromo-3-nitrilopropionamide (DBNPA), 2-bromo-2-nitropropane-1,3-diol (Bronopol), 5-chloro-2-methyl-4-isothiazolin-3-one (OMIT), n-alkyl dimethyl benzyl ammonium chloride, didecyl dimethyl ammonium chloride (DDAC), alkenyl dimethylethyl ammonium chloride, tetrakis hydroxymethyl phosphonium sulfate (THPS). The use of these biocides provides the advantage that in process water they all are capable of quick inactivation of microorganisms.

In one embodiment the biocide is 2,2-dibromo-2-cyanoacetamide (also called as 2,2-dibromo-3-nitrilopropionamide or dibromonitrilopropionamide, DBNPA), which is a white crystalline powder having melting point of 124.5° C., water solubility about 15 000 mg/l at 20° C. and vapor pressure 9.00 E-4 mm of Hg at 20° C. DBNPA hydrolyzes easily under both acidic and alkaline conditions. Although DBNPA is compatible with many chemical classes, including oxidizing agents, it will react readily with nucleophilic agents and sulfur-containing reducing agents. DBNPA is a non-oxidizing biocide and it is not a bromine-release biocide. DBNPA does act similar to the typical halogen biocides. The reaction of DBNPA with sulfur-containing nucleophiles common to microorganisms, such as glutathione or cysteine, is the basis of its mode of antimicrobial action. Unlike other thiol-reactive biocides, its action is such that thiol-based amino acids, such as cysteine, are oxidized beyond the formation of disulfide species. This reaction irreversibly disrupts the function of cell-surface components, interrupting transport across cell membranes, and inhibiting key biological functions.

The carrier has generally low solubility to water, such as about 10-15% (at 20° C.), or less than about 5%, or even less than about 1%. Generally the carrier does not form a separate phase in water, but it may form a colloid. However, the biocide should be substantially soluble to the carrier, but it should not react chemically with the carrier, so the biocide substantially retains its activity. The composition thus formed is stable or substantially stable at least for weeks or months, and it does not decompose or release harmful compounds. The carrier may be present as a carrier composition containing more than one ingredient. In one embodiment the carrier composition comprises a surfactant. In one embodiment the carrier composition comprises a stabilizing agent. The carrier should have both hydrophilic and hydrophobic properties, i.e. it should have a surfactant-like "soapy" structure and/or properties. In one embodiment the carrier is a defoamer.

Defoamer (defoaming agent) is a substance generally used to reduce foaming due to gases, nitrogenous materials or proteins, which may interfere with processing. General examples of defoamers include long chain fatty alcohols, organic phosphates, silicone fluid etc. In the invention the defoamer also facilitates the solubility of the biocide. If there are foaming compounds in the biocide composition, such as surfactants, it may be advantageous also to add defoaming agents to the composition.

The defoamer may be present as a defoamer composition containing more than one ingredient. The biocide composition as a whole may also be defined as a biocide composition comprising a biocide and one or more other ingredients, such as the defoamer ingredients described herein. In one embodiment the carrier or the defoamer comprises a polyethylene glycol (PEG) ester. In one embodiment the carrier or the defoamer comprises a polyethylene glycol ester having surfactant activity i.e. containing also a hydrophobic moiety. The hydrophobic moiety may be a fatty acid, such as a non-water soluble fatty acid or low-water soluble fatty acid.

In one embodiment the polyethylene glycol ester is a fatty acid polyethylene glycol ester. In one embodiment the polyethylene glycol ester is a tall oil fatty acid polyethylene glycol ester. In one embodiment the molecular weight of the polyethylene glycol is in the range of about 300 to 100 000 Daltons. In one embodiment the molecular weight of the polyethylene glycol is in the range of about 300 to 50 000 Daltons, such as in the range of about 300 to 10 000 Daltons. In one embodiment the polyethylene glycol ester is a tall oil fatty acid PEG 300 ester (the number indicating the average molecular weight of the polyethylene glycol in Daltons). In one embodiment the biocide composition contains about 20-50% (w/w) of the polyethylene glycol ester. In one embodiment the biocide composition contains about 30-50% (w/w) of the polyethylene glycol ester. In one embodiment the biocide composition contains about 33-46% (w/w) of the polyethylene glycol ester.

Basically, the amount of carrier in the biocide composition is advantageously as high as possible to ensure good stability and to effectively transport the biocide to the point of application. However, the upper limit needs to be low enough to be able to incorporate enough active biocide and possibly other auxiliary agents such as mineral oil and surfactant, into the biocide composition. The amount of 50% by weight was found to satisfy these requirements. On the other hand, if the amount of carrier, such as polyethylene glycol (PEG) ester, was less than 20% by weight the stability of the micelles formed by the biocide and the carrier tends to decrease and the transport of biocide onto the sliming surfaces becomes clearly less efficient. An optimal biocide composition in terms of solubility of the biocide into the carrier micelle, long time storage stability, such as up to 3 months, may be obtained with a carrier amount of about 40%, such as 33-46% by weight.

In one embodiment the weight ratio of the defoamer to the biocide is from 1.9:1 to 5:1. The solubility of the biocide into the carrier limits the upper ratio and the total amount of the components needs to be adjusted to be able to incorporate further auxiliary agent. In another embodiment the weight ratio of the defoamer to the biocide is from 2:1 to 3:1, more or even from 2:1 to 2.5:1.

In one embodiment the biocide composition, the carrier or the defoamer composition further comprises oil, such as mineral oil or synthetic oil. In one embodiment the biocide composition contains about 20-30% (w/w) of mineral oil. In one embodiment the biocide composition contains about 23-28% (w/w) of mineral oil. In one specific example the biocide composition contains about 25% (w/w) of mineral oil. In one embodiment the biocide composition contains about 30-50% (w/w) of polyethylene glycol ester and 20-30% (w/w) of mineral oil. In one specific example the biocide composition contains about 46% (w/w) of polyethylene glycol ester, such as tall oil fatty acid PEG 300 ester, and about 25% (w/w) of mineral oil. The mineral oil may be any suitable type of conventional mineral oil used in defoamers, such as a base oil, for example mineral oil type AP/E core 150 or the like. Base oil is the name given to lubrication grade oils initially produced from refining crude oil (mineral base oil) or through chemical synthesis (synthetic base oil). Base oil is typically defined as oil with a boiling point range between 288 and 566° C. (550 and 1050° F.), consisting of hydrocarbons with 18 to 40 carbon atoms. This oil can be either paraffinic or napthenic in nature depending on the chemical structure of the molecules. Group I base stocks contain less than 90 percent saturates and/or greater than 0.03 percent sulfur and have viscosity index greater than or equal to 80 and less than 120.

Viscosity index is an empirical, unitless number indicating the effect of temperature change on the kinematic viscosity of an oil. Liquids change viscosity with temperature, becoming less viscous when heated; the higher the viscosity index of an oil, the lower its tendency to change viscosity with temperature. The mineral oil may have a viscosity in the range of about 1000-1500 (ASTM D5293), such as about 1250 for AP/E core 150. The viscosity index (ASTM D2270) may be in the range of 50-150, more particularly 80-120, such as about 100 for AP/E core 150. The mineral oil may be solvent neutral.

Surfactants are usually organic compounds that are amphiphilic, meaning they contain both hydrophobic groups (their tails) and hydrophilic groups (their heads). Therefore, a surfactant contains both a water insoluble (or oil soluble) component and a water soluble component. Surfactants will diffuse in water and adsorb at interfaces between air and water or at the interface between oil and water, in the case where water is mixed with oil. The insoluble hydrophobic group may extend out of the bulk water phase, into the air or into the oil phase, while the water soluble head group remains in the water phase. This alignment of surfactants at the surface modifies the surface properties of water at the water/air or water/oil interface.

In one embodiment the biocide composition, the carrier or the defoamer composition further comprises a surfactant. In one embodiment the surfactant is dioctyl sodium sulfosuccinate. In one embodiment the biocide composition contains about 20-40% (w/w) of dioctyl sodium sulfosuccinate. In one embodiment the biocide composition contains about 25-35% (w/w) of dioctyl sodium sulfosuccinate. In one specific example the biocide composition contains about 27% (w/w) of dioctyl sodium sulfosuccinate. In one specific example the biocide composition contains about 33% (w/w) of tall oil fatty acid PEG 300 ester and about 27% (w/w) of dioctyl sodium sulfosuccinate.

The oil and surfactant decrease the foaming tendency and aid in loading the biocide into the carrier. The most efficient transport effect of the biocidal composition is advantageously obtained using an auxiliary surfactant in the amount of at least 20% by weight. The upper limit is restricted by the amount of biocide and carrier to be used.

The biocide composition, the carrier or the defoamer composition may further comprise a stabilizing agent. The stabilizing agent may be a chemically stabilizing agent or a physically stabilizing agent. Examples of such stabilizing agents include myristates, surfactants and organic acids. In one embodiment the organic acid is citric acid. The concentration of the citric acid in the biocide composition may be about 0.1-2% (w/w), such as about 0.1-0.5% (w/w), for example about 0.2% (w/w).

In one embodiment the stabilizing agent is isopropyl myristate. In one embodiment the biocide composition contains about 10-15% (w/w) of isopropyl myristate. In one specific example the biocide composition contains about 13% (w/w) of isopropyl myristate.

The present invention also provides a method for targeting a biocide onto a biofilm surface in an aqueous environment, comprising providing the biocide composition, and contacting said biofilm surface with said biocide composition. The surface may be for example a plastic surface or a metal surface, such as steel, stainless steel, or copper surface.

The present invention also provides methods for treating water, comprising providing the biocide composition, and adding or dosing said biocide composition to the water. The methods aim for eliminating and/or preventing biofilm formation on surfaces to clean and/or remove the forming or already formed slimes or biofilms. "Dosing" generally refers to adding or feeding chemicals in quantities into a process fluid continuously or at intervals to give sufficient time for the chemical to react or show the results.

The biocide composition as used in the methods described herein may be added to the water to be treated in biostatic or biocidal amounts. Biostatic amount refers to an amount sufficient to at least inhibit the activity and/or growth of the microbes or the biofilm. Biocidal amount refers to more effective activity, such as to an amount capable of killing most or all of the microbes.

The present invention also provides a method for controlling biofilms by eliminating microorganisms and/or preventing the growth thereof in an aqueous environment, comprising providing the biocide composition, and adding or dosing said biocide composition to the aqueous environment. The "aqueous environment" as used herein refers to a water system, such as an industrial water system, containing aqueous solution. The eliminating and/or preventing refer to any biostatic or biocidal effect, such as killing, reducing, removing, or inhibiting the growth of, or inactivating or cleaning the biofilm. The elimination may be total or partial. The prevention refers to any preventive eliminating action which reduces or inhibits the growth of the microorganisms and thereby totally or partially prevents the formation of the biofilm.

The present invention also provides the use of said biocide composition for controlling (for example eliminating, inactivating and/or preventing) biofilms or microorganisms in aqueous processes. In one embodiment the microorganisms are in a form of a biofilm. This results in a synergy in controlling of attached microorganism (biofilms) on surfaces.

"Aqueous solution" as used herein refers to any solution containing water. Said aqueous solution is generally any solution containing sufficient amount of water phase to be used in the current application. Said aqueous solution may be for example water, ground water, surface water, waste water, industrial water, industrial raw water, sludge or solids suspension, pulp suspension or any other suitable aqueous solution.

The aqueous environment may be an industrial process, such as a water treatment process. The industrial process may be selected from processes such as wood pulp, paper, board, industrial wastewater treatment, oil drilling, machine tool industry, oils cutting tools, hydraulics, etc. and the equipment used in such processes. The application target may be for example any industrial water system, which generally means an engineered recirculating water system, such as papermaking system, cooling water systems (e.g. cooling towers, open and closed loop cooling units), industrial raw water systems, drinking water distribution systems, sanitizing drinking water system, oil production or recovery systems (oil field water system, drilling fluids), fuel storage system, metal working systems, heat exchangers, reactors, equipment used for storing and handling liquids, boilers and related steam generating units, radiators, flash evaporating units, refrigeration units, reverse osmosis equipment, gas scrubbing units, blast furnaces, sugar evaporating units, steam power plants, geothermal units, nuclear cooling units, water treatment units, pool recirculating units, mining circuits, closed loop heating units, machining fluids used in operations such as for example drilling, boring, milling, reaming, drawing, broaching, turning, cutting, sewing, grinding, thread cutting, shaping, spinning and rolling, hydraulic fluids, cooling fluids, and the like.

In one embodiment the biocide composition is added or dosed to a pulp and/or paper processing system. The composition may be generally utilized throughout the system to minimize and to prevent biofilm formation on the system surfaces. The composition may be added at almost any point in the system to generally maintain microbe control throughout the system. In certain examples the composition is added in a short loop of the system. Other examples of suitable adding points are large storage towers for process water (circulating water towers, filtrate water towers), clear or cloudy filtrate storage tanks, pulpers or process streams upstream/downstream of the pulpers, broke system or process streams up-stream/downstream of vessels therein, wire pit process streams up-stream/downstream of the pit, paper machine blend chest process streams up-stream/downstream of the chest, fresh water tank, warm water tank and shower water tank.

The composition of the invention may be added as a solid, such as dry powder, or more generally in a liquid form to the liquid or water to be treated. It may be dosed continuously or periodically as a batch process. Examples of suitable concentrations to be used in the processes are about 1-50 ppm, more particularly 1-10 ppm, such as 3-7 ppm. The composition may be fed for about 3-45 minutes each about 6-24 times a day, or for example for about 10-30 minutes for about 12-24 times a day.

The advantage in using the biocide composition of the present disclosure is that a defoaming effect is obtained in addition to the biocidal effect. Moreover, less biocide is required to provide the same biocidal effect compared to regular biocidal compositions without a defoaming agent as a carrier. In a favourable composition the amount of biocide may be reduced down to 1/10, or even 1/20 of the amount needed without defoamer in the composition. The use of defoamer boosts the biocidal effect of the biocide when solubilized into the defoamer carrier. The carrier loaded with the biocide is able to withstand ambient conditions and variations therein thus increasing the stability of the composition. The biocidal effect at the critical positions prone to biofilm formation is enhanced. Especially, the liquid-air interfaces of the process tanks which typically tend to collect the most biofilm and which are difficult positions to clean are effected using the biocide composition of the present disclosure comprising both the biocide and the defoamer carrier. Furthermore, in using the combination of the biocide and the defoamer no additional chemical is necessary for providing the enhanced biocidal effect. This means that, for example, less equipment such as chemical tanks are needed and the processing becomes more cost-effective.

The present invention also provides a method for preparing said biocide composition comprising providing a biocide and a biocide carrier, and mixing said biocide and said carrier to obtain said biocide composition.

Next the invention will be described in detail with reference to the following non-limiting examples.

EXAMPLES

Indicative Solubility of DBNPA on Different Defoamer Products

Different aqueous defoamer compositions A, B, C, and D were indicatively tested for their solubility and reactivity with DNBPA.

Defoamer A contains a reaction product (an ester) of its ingredients, tall oil fatty acid and polyethylene glycol 300, namely tall oil fatty acid PEG 300 ester (TOFA-PEG300). Defoamer D contains only a mixture of its ingredients dioctyl sodium sulfosuccinate (DOSS, a surfactant) and free tall oil fatty acid. It does not contain any tall oil fatty acid PEG ester. Both Defoamers B and C contain Defoamer A (TOFA-PEG300), and other ingredients.

DBNPA is soluble in Defoamer A, but also reacts with it. The product was a physically stable solution but a gradual decomposition of DBNPA occurred which was noticed by the solution color turning dark brown and by liberation of (toxic) bad smelling odors within a few hours or days. DBNPA is not very soluble in Defoamer D.

However, DBNPA is soluble in Defoamers B and C, but it does not react with them. No gradual change in visual appearance was noticed at least within several weeks. Defoamers B and C seem suitable carriers for DBNPA.

Based on these preliminary tests compositions 1 and 2 were prepared for the biocidal efficacy test.

Composition 1

The composition 1 is a blend of a defoamer composition and DBNPA (a biocide). A minor reaction between the biocide and the tall oil fatty acid PEG 300 ester may have taken place during the blending.

|  | g | w-% |
|---|---|---|
| Tall oil fatty acid PEG 300 ester | 7.62 | 46 |
| Mineral oil (solvent neutral 150) | 4.16 | 25 |
| DBNPA (biocide) | 2.45 | 14.8 |
| Isopropyl myristate (C14 fatty acid isopropyl ester) | 2.08 | 13 |
| Citric acid | 0.25 | 1.50 |
| total | 16.574 | 100 |

Composition 2

The composition 2 is a blend of a defoamer composition and DBNPA (a biocide). A minor reaction between the biocide and the tall oil fatty acid PEG 300 ester may have taken place during the blending.

|  | g | w-% |
|---|---|---|
| Tall oil fatty acid PEG 300 ester | 5.01 | 33 |
| Dioctyl sodium sulfosuccinate | 4.14 | 27 |
| Water | 3.39 | 22 |
| DBNPA (biocide) | 2.44 | 16.1 |
| Citric acid | 0.23 | 1.52 |
| total | 15.216 | 100 |

Test Results for Biocidal Efficacy

The test method used is described in WO2005045132. It measures efficacy of products in inactivation of a pre-formed thin biofilm on a stainless steel surface. This "Hedgehog" method is a biofilm specific three-step analysis. It can be used for rapid efficacy testing of anti-biofilm agents. Different products can be compared for their efficacy in inactivation and/or removal of pre-existing biofilms.

In step A the Hedgehog plate is immersed in flowing process water. True primary-biofilm formers are allowed to form a film on the plate. In step B the plate is ex-posed to different anti-biofilm agents in the white water (circulating water of a paper machine). The product concentration and duration of the exposure can be freely varied. In step C the viability of the remaining biofilms is analyzed. The amount of new biofilm indicates the efficacy in inactivation of the pre-grown biofilm, i.e. more survivors create more biofilm. This is based on a phenomenon called biotransfer.

Test environment was paper machine white water. Dosages are indicated ppm (mg/l) as product. Fennosan R20V is a commercial product containing DBNPA only (20% a.i., active ingredient).

|  | ppm (mg/l as product) | Amount of viable biofilm (staining and visual quantification) |
|---|---|---|
| Results 23.5.2012 | | |
| Reference (untreated) | | ++(+) |
| R20V | 1 | ++ |
|  | 2 | +++ |
|  | 5 | + |
|  | 10 | + |
| Composition 1 | 0.5 | − |
|  | 2 | − |
| Composition 2 | 0.5 | + |
|  | 2 | (+) = very weak |
| Results 8.6.2012 | | |
| Reference (untreated) | | ++ |
| R20V | 1 | +++ |
|  | 2 | + |
|  | 5 | +++ |
|  | 10 | +++ |
| Composition 1 | 0.5 | (+) = very weak |
|  | 2 | (+) = very weak |
| Composition 2 | 0.5 | + |
|  | 2 | (+) = very weak |

Test Results for Foaming Tendency

Composition 1 and Composition 2 performance was tested in a foaming test in tap water at 50° C. with dosages of 10 µl to 160 µl. Composition 1 did not cause foaming, in contrast to the reference biocide product Fennocide Quat 40 (DDAC, a quaternary ammonium biocide) which did cause plenty of foaming. Composition 2 was foaming, but if taking into account the relative biocidal efficacy, i.e. a much lower dosage is needed than with the reference biocide, also this result was good. The test results for foaming tendency using Composition 1, Composition 2 and Fennocide Quat 40 as a reference are shown in FIG. 1.

The invention claimed is:

1. A biocide composition for industrial water systems comprising a biocide and a carrier, the biocide being soluble in the carrier and the carrier being a defoamer and comprising polyethylene glycol ester, and said biocide composition further comprising a stabilizing agent and a surfactant, or a mineral oil, or both wherein the stabilizing agent is isopropyl myristate and the surfactant is dioctyl sodium sulfosuccinate.

2. The biocide composition of claim 1, wherein the polyethylene glycol ester is a fatty acid polyethylene glycol ester.

3. The biocide composition of claim 2, wherein the polyethylene glycol ester is a tall oil fatty acid polyethylene glycol ester.

4. The biocide composition of claim 1, wherein the composition further comprises an organic acid.

5. The biocide composition of claim 1, wherein the biocide composition contains 20-50% (w/w) of the polyethylene glycol ester.

6. The biocide composition of claim 1, wherein the biocide composition contains 20-30% (w/w) of the mineral oil.

7. The biocide composition of claim 1, wherein the biocide composition contains 20-40% (w/w) of the dioctyl sodium sulfosuccinate.

8. The biocide composition of claim 1, wherein the biocide composition contains 10-20% (w/w) of the biocide.

9. A method for controlling biofilms by eliminating and/or preventing microorganisms in an aqueous environment, said method comprising the steps of:
a) providing the biocide composition of claim 1, and
b) dosing said biocide composition to the aqueous environment.

10. The method of claim 9, wherein the aqueous environment is an industrial water system.

11. The method of claim 10, wherein the industrial water system is selected from papermaking system, cooling water systems selected from cooling towers and open and closed loop cooling units, industrial raw water system, drinking water distribution systems, sanitizing drinking water system, oil production or recovery systems, fuel storage system, metal working systems, heat exchangers, reactors, equipment used for storing and handling liquids, boilers and related steam generating units, radiators, flash evaporating units, refrigeration units, reverse osmosis equipment, gas scrubbing units, blast furnaces, sugar evaporating units, steam power plants, geothermal units, nuclear cooling units, water treatment units, pool recirculating units, mining circuits, closed loop heating units, machining fluids used in drilling, boring, milling, reaming, drawing, broaching, turning, cutting, sewing, grinding, thread cutting, shaping, spinning and rolling, hydraulic fluids, and cooling fluids.

12. The method of claim 9 wherein the biocide composition is dosed to a concentration of 1-50 ppm.

13. The biocide composition of claim 4, wherein the organic acid is citric acid.

14. The biocide composition of claim 1, wherein the biocide is a non-oxidizing biocide.

15. The biocide composition of claim 14, wherein the biocide is selected from glutaraldehyde, 2,2-dibromo-3-nitrilopropionamide (DBNPA), 2-bromo-2-nitropropane-1,3-diol, 5-chloro-2-methyl-4-isothiazolin-3-one (CMIT), 2-methyl-4-isothiazolin-3-one (MIT), a mixture of CMIT and MIT, 1,2-dibromo-2,4-dicyanobutane, bis(trichloromethyl)sulfone, 2-bromo-2-nitrostyrene, 4,5-dichloro-1,2-dithiol-3-one, 2-n-octyl-4-isothiazolin-3-one, 1,2-benzisothiazolin-3-one, ortho-phthalaldehyde, quaternary ammonium compounds selected from n-alkyl dimethyl benzyl ammonium chloride, didecyl dimethyl ammonium chloride (DDAC) or alkenyl dimethylethyl ammonium chloride, guanidines, biguanidines, pyrithiones, carbamates, 3-iodopropynyl-N-butylcarbamate, phosphonium salts selected from tetrakis hydroxymethyl phosphonium sulfate (THPS), 3,5-dimethyl-1,3,5-thiadiazinane-2-thione, 2-(thiocyanomethylthio) benzothiazole, methylene bisthiocyanate (MBT), and combinations thereof.

* * * * *